(12) United States Patent
Buchwald et al.

(10) Patent No.: US 9,057,707 B2
(45) Date of Patent: Jun. 16, 2015

(54) DETECTION SYSTEM AND INSPECTION METHOD FOR BOTTLE SEAM AND EMBOSSING ALIGNMENT

(75) Inventors: Carsten Buchwald, Bad Breisig (DE); Wolfgang Schorn, Honningen (DE)

(73) Assignee: KHS GmbH, Dortmund (DE)

( * ) Notice: Subject to any disclaimer, the term of this patent is extended or adjusted under 35 U.S.C. 154(b) by 144 days.

(21) Appl. No.: 13/811,731

(22) PCT Filed: May 18, 2011

(86) PCT No.: PCT/EP2011/002491
§ 371 (c)(1),
(2), (4) Date: Jan. 23, 2013

(87) PCT Pub. No.: WO2012/010231
PCT Pub. Date: Jan. 26, 2012

(65) Prior Publication Data
US 2013/0120746 A1    May 16, 2013

(30) Foreign Application Priority Data
Jul. 23, 2010   (DE) .......................... 10 2010 032 166

(51) Int. Cl.
| G01N 21/00 | (2006.01) |
| G01N 21/90 | (2006.01) |
| G01B 11/25 | (2006.01) |
| G01B 11/27 | (2006.01) |

(52) U.S. Cl.
CPC ............ *G01N 21/9036* (2013.01); *G01B 11/25* (2013.01); *G01B 11/272* (2013.01); *G01N 21/9045* (2013.01)

(58) Field of Classification Search
CPC .............. G01N 21/90; G01N 21/9045; G01N 21/9054; G01N 21/9036; G01N 21/00
USPC .................................. 356/239.4, 239.7, 240.1
See application file for complete search history.

(56) References Cited

U.S. PATENT DOCUMENTS

| 3,814,521 | A |   | 6/1974 | Free |
| 6,452,156 | B2 | * | 9/2002 | Lindner .................... 250/223 B |
| 6,621,569 | B2 | * | 9/2003 | Sones ......................... 356/237.2 |
| 7,488,965 | B2 | * | 2/2009 | Cochran et al. .......... 250/559.45 |
| 7,924,421 | B2 | * | 4/2011 | Schmidt et al. ............ 356/239.4 |

(Continued)

FOREIGN PATENT DOCUMENTS

| DE | 100 17 126 C1 | 6/2001 |
| DE | 10 2006 008 840 B4 | 5/2009 |

(Continued)

*Primary Examiner* — Roy M Punnoose
(74) *Attorney, Agent, or Firm* — Occhiuti & Rohlicek LLP

(57) ABSTRACT

A system for detecting features on a container wall includes an optical assembly comprising a camera, and an illuminating unit having light sources arranged on conductive tracks. Viewed in a vertical direction of the unit, the light sources are in vertical columns to project a strip-shaped beam onto a container-wall region. When viewed axially, the light sources are arranged on the conductive track one above the other without offset. Each column of light sources is actuated to project a light pattern on the container-wall region that can be variably adjusted as a function of surface properties of the container-wall region. The illuminating unit has first and second light source sets in corresponding adjacent vertical columns. Each light source set has one or more light sources. Adjustment is effected by concurrently switching the first and second light source sets between an on-state and an off-state.

18 Claims, 14 Drawing Sheets

(56) References Cited

U.S. PATENT DOCUMENTS

| | | | |
|---|---|---|---|
| 2005/0174571 A1* | 8/2005 | Cochran et al. | 356/240.1 |
| 2010/0118138 A1* | 5/2010 | Djachiachvili | 348/125 |
| 2012/0130677 A1* | 5/2012 | Wolfe et al. | 702/173 |
| 2013/0083330 A1* | 4/2013 | Piana et al. | 356/614 |

FOREIGN PATENT DOCUMENTS

| | | |
|---|---|---|
| DE | 10 2008 018 096 A1 | 11/2009 |
| DE | 10 2008 053876 A1 | 5/2010 |
| DE | 10 2008 064 562 | 7/2010 |
| EP | 1 446 656 B1 | 9/2009 |
| EP | 2 251 268 A2 | 11/2010 |
| EP | 2 287 593 A1 | 2/2011 |
| GB | 2 334 576 A | 8/1999 |
| GB | 2334576 B * | 3/2002 |
| GB | 10 2008 018 096 A1 | 11/2009 |
| JP | 08015163 A | 1/1996 |
| JP | 10068612 A | 3/1998 |

\* cited by examiner

US 9,057,707 B2

DETECTION SYSTEM AND INSPECTION METHOD FOR BOTTLE SEAM AND EMBOSSING ALIGNMENT

CROSS REFERENCE TO RELATED APPLICATION

This application is the national phase under 35 USC 371 of international application no. PCT/EP2011/002491, filed May 18, 2011, which claims the benefit of the priority date of German application no. 10 2010 032 166.4, filed Jul. 23, 2010. The contents of the aforementioned applications are incorporated herein in their entirety.

FIELD OF DISCLOSURE

The invention relates to a detection system for detecting bottles and similar containers which exhibit features arranged on a container wall, with the detection system having at least one illuminating unit and at least one optical assembly having at least one camera, with the illuminating unit exhibiting a plurality of light sources arranged on a plurality of conductive tracks, the light sources being arranged one above the other when viewed looking in the vertical direction of the illuminating unit, such that by means of the light sources arranged in vertically aligned columns a strip-shaped light beam can be projected onto a container wall region, with the respective light beams projected onto the container wall region being spaced apart from each other when viewed looking in an axial direction of the illuminating unit. The invention also relates to an inspection method which comprises such a detection system.

BACKGROUND

DE 10 2006 008 840 B4 discloses an illuminating device for detecting defects on the surface of a cylindrical object. A slit diaphragm is arranged inside a lamp. The slit diaphragm is a cylinder equipped with axially extending slits.

JP 08015163 A is also concerned with an inspection device for cylindrical objects. A plurality of light sources is arranged each on either side of a conveyor. Cameras are arranged between the light sources. The plurality of light sources generate a strip pattern on the periphery over the entire height of the cylindrical object and which is recorded by the cameras.

JP 10068612 A describes a method by which a surface of an object can be examined without the object having to be rotated. This is done by irradiating the object at a given angle with laser light beams which are reflected by the surface of the object onto a screen.

U.S. Pat. No. 3,814,521 discloses a method for detecting an object onto which a light pattern is cast. The light pattern is generated by placing a light source behind a grid so that illuminated and non-illuminated regions are created on the object by way of the grid. A camera "looks" through an angled mirror at the object onto which a light pattern has been cast in this way.

EP 1 446 656 B1 describes a method for inspecting containers by which damaged containers can be detected and separated out, although with acceptable irregularities entering the evaluation. The containers are illuminated from below or from above.

DE 10 2008 018 096 A1 is intended to provide a method with which scratch marks on containers or irregularities in the interior of the container wall are to be detectable. To this end, a regular texture which may be a strip or grid pattern is applied to the container wall. With certain combinations it is also possible to determine the flatness or surface ripple. The textured area is a plane but it may also be curved, whereby the pattern is predetermined. The textured area can be transilluminated from behind or irradiated with light using the reflected-light method so that transmitted or reflected light reaches the container.

Containers of the type referred to above can be used in the manner of bottles or similar for liquids, for example for drinks. The containers can consist of a transparent, translucent or opaque material, for example glass, or of a translucent plastic such as PET, and preferably exhibit a shiny surface. The containers can be filled with filling media of very different kinds and can exhibit different colours. The containers are for example fed to a labelling machine in which a label is to be applied in a predetermined and repeatable position always aligned the same way relative to external position features or design features or embossings on the outside of the container. As well as being correctly aligned on embossings or other features however, the label should also be arranged on the container as free from wrinkles as possible and with no elevations and/or depressions. Containers can however also exhibit two vertically extending bottle seams arranged directly opposite each other or only a single bottle seam. To this extent it is thoroughly desirable for the label not to be applied to one of the bottle seams or on the bottle seam or container seam since this impairs the appearance of the label or container in so far as the label can display a fold (elevation/depression) in the region of the bottle seam, giving the impression of the label having been applied to the container with poor quality. This can lead to end consumers avoiding the product.

These are problems addressed for example by DE 10 2008 053 876 A1, which goes back to the applicant, with its illuminating unit exhibiting a plurality of light sources and being configured so that the respective light source projects a strip-shaped light beam onto a container wall region, with the strip-shaped light beams that are projected onto the container wall region being spaced apart from one another. Bottle seams or embossings can be easily detected in this way; an application of labels on bottle seams can be avoided or labels that are to be applied can be applied aligned to embossings. It has been shown however that containers can exhibit different surface properties, i.e. surface properties which differ from the preferably shining surface and which can lead to the corruption of for example the bottle seam detection. Thus containers can for example exhibit a dull and/or rough surface, resulting in an out-of-focus projected strip pattern. Thus bottle seams for example may not be correctly detected because the projected strip pattern is very unclear due to the dull and/or rough surface.

SUMMARY

The object of the invention therefore is to provide a detection system and an inspection method of the above-mentioned type which with simple means detects features on the container even when containers of different surface quality are to be inspected and so that the label cannot be applied to a bottle seam and/or can be arranged correctly aligned to embossings on the container.

Provision is advantageously made such that the light sources of each conductive track which are arranged in vertically aligned columns are, when viewed in the axial direction, arranged on said conductive track above one another without offset; each vertically aligned column of light sources of the respective conductive track can be operated by a control unit as a function of detected surface properties of the container such that the vertically aligned columns are able to project onto the container wall region a light pattern which can be variably adjusted as a function of the surface properties.

By these simple means therefore it is possible to project onto the container wall, without the need for a statically, unchangeably predetermined light pattern, a variably producible light pattern onto the container wall region [sic], in which adjacent columns of light sources are combined in preferred embodiment to form as it were a block of light which is spaced apart from the next block of light by a non-illuminated section, etc. Despite poor surface quality, disturbances in the block of light caused for example by a bottle seam can therefore be easily detected in this way because now only the block of light is viewed and no longer individual light beams. It is of course also possible to generate a type of light pattern in which alternating columns of light sources are switched on and off so that it is not blocks of light which are projected onto the container wall region but actually interspaced strips of light which however have a relatively large space between one another because of the non-activation of immediately adjacent columns of light sources. The decision as to which of the advantageous light patterns is generated is therefore taken directly by the detecting of the surface quality.

In a favourable version, the illuminating unit is configured so that vertically aligned light beams are projected onto the container wall region.

In an initial embodiment of the illuminating unit it is advantageously provided for it to exhibit a carrier element having a light surface oriented to the container. In a preferred embodiment the conductive tracks on which the light sources are disposed in vertical orientation and interspaced can be arranged on the light surface. Each conductive track is preferably flexible, i.e. it can bend, and exhibits vertically arranged recording strips for the light sources such that a strip-shaped pattern is projected onto the container wall region. The light sources can be executed as for example LED light sources. The light sources can of course also be executed as infrared light source. The light sources are preferably pulsed, with the optical assembly or the at least one camera being synchronised with the light source.

In an advantageous embodiment the carrier element or the light surface is executed in the shape of a sector of a circle which at least partly surrounds the container that is to be inspected and/or detected but is axially spaced from it. On the light surface the plurality of conductive tracks with light sources arranged thereon are arranged above one another; the individual light source rows or light source strips of one conductive track are advantageously arranged without any lateral offset relative to the light source rows or light source strips of the next following conductive track which are disposed beneath them.

In an advantageous embodiment the optical assembly exhibits multiple, preferably three, cameras which are favourably arranged relative to the strip pattern projected onto the container wall region so that the entire container wall region irradiated by the light sources can be recorded. In a favourable embodiment, at least a region of approx. 40% of the total periphery of the container can be recorded by the optical assembly. The optical assembly is of course advantageously vertically offset relative to the illuminating unit.

It is also conceivable however for two illuminating units arranged one above the other to be provided, between which the at least one camera is disposed. Both illuminating units or their columns of light sources can be operated identically or differently to generate identical or different light patterns.

The detection system is preferably associated with a labelling machine which exhibits a labelling star wheel. To this extent, in the case of the embodiment with the labelling star wheel, the carrier element and optical assembly can be executed depending on the structural layout of the labelling star wheel. This means that only a certain container wall region can be irradiated by the illuminating unit and recorded by the optical assembly. It is advantageous when a container wall region which is arranged in a transition from a basic body to the neck region is irradiated with the variably producible light pattern. The container wall region concerned is therefore limited in both peripheral direction and vertically. It is therefore advantageous for the purpose of the invention if the carrier element is executed for example as a curved sheet metal strip so that it does not impinge on the circular path of the container or of the labelling star wheel. The carrier element can of course also be made of other suitable materials. The conductive track(s) can be fixed in a stable position to the carrier element in a suitable manner, for example by bonding on their backs, to name just one exemplary method of attachment.

In another favourable embodiment, an optical lens, preferably in the embodiment as a cylindrical lens, may be disposed in front of the at least one camera, preferably in front of all cameras, in order optically to spread the strip pattern that is projected onto the container wall region, or the vertical line structure, over the entire vertical detection region. The optical lens may also be executed as a Fresnel lens, to name just one other suitable example of an optical lens.

A higher optical resolution of the detection system can be achieved by way of the advantageously provided optical lens because the line structure spreads out far more finely over the entire detection region of the optical detection system, and this makes sense for shining bottle surfaces, for example. The invention can dispense with an optical lens however because the strips of light are combined to form as it were blocks of light.

Because of the special actuating of the individual light sources (strips or columns), a vertical strip pattern selectively dependent on, and adjustable for, surface properties is projected onto the container body or container wall region. The advantageous actuating of the light sources generates an image of the entire illuminating unit or its actuated light sources in strips of vertically arranged lines. If no changes such as a bottle seam for example are present on the container wall or on a container wall region that is to be inspected, then the lines or blocks of light are always aligned the same way relative to one another in number, irrespective of container rotations or container positions. If the bottle seam now encroaches on this line or block pattern, their relative number and/or arrangement will change. There will be a change in the line image or block image for example. In this way therefore an absolutely accurate position of the container seam can be advantageously determined with the invention irrespective of surface quality, container contents and container colour. Two detection systems one after the other can be provided in a favourable manner such that exact determining of the container seam position is ensured by rotating the container, this also because the detection system should not impinge on a labelling star wheel, if one is provided, especially by its carrier element as described above. By rotating the container, a further container wall region can be inspected with the following second detection system. Here the invention is based on the fact that the container stands upright on a rotatable turntable and can be turned as it is fed to the detection system.

To avoid any adverse effect on the detection accuracy by reflections of the container being incident through the environment, the light sources can be executed as infrared light source in which case a daylight blocking filter may also be provided.

It is possible, by way of detecting or determining the position of the container seam in the incident-light method, to align the container to allow a label to be attached at places where there is no container seam, thereby avoiding label elevations (folds) for example.

In order to detect the container seam or locate it accurately in its position even when a container having a dull or rough surface, i.e. actually detrimental surface properties, are [sic] to be inspected, it is therefore advantageously provided for the surface properties of the container to be detected first. With the detected surface properties, which are preferably fed into a control unit, the vertically aligned columns of light sources are then selectively operated so that the light sources/columns project a light pattern onto the container wall region which is variably adjusted as a function of the surface properties.

By a simple operating of the columns it is therefore possible to generate different light patterns whose individual lines or blocks exhibit a greater relative axial spacing compared with a light pattern with all columns operated, such that even containers with a dull and/or rough surface can be examined sufficiently conclusively. The individual lines may be blurred but a block formation of the individual strips of light is generated from which disturbances in the individual block can be detected. A block may be formed for example from two, three or four adjacent strips of light which are operated/switched on by the control unit. The next two, three or four strips of light (columns of light sources) are operated such that they are switched off, i.e. do not light up. This procedure is applied alternately to each of the following strips of light to generate the light pattern. The large distance of the individual blocks relative to one another because of the activated/deactivated "blocks of light" is thus apparent. Of course more than four consecutive strips of light can be actuated in this way. Instead of the identical number of activated and deactivated consecutive strips of light, different numbers may be selected. Thus for example four consecutive strips of light can be activated, i.e. can light up pulsatingly, with only the following two strips of light being switched off so as to create a non-illuminated region, followed again by four consecutive activated strips of light etc. To this extent therefore the invention should cover all light patterns that are conceivable and suitable for the respectively detected surface property.

It is also advantageous if blocks of lines are generated in which all strips of light arranged directly one above the other and adjacent in selected number light up pulsatingly while the adjacent strips of light remain switched off. This will generate a light pattern comprising a plurality of illuminated "blocks of lines" which are interspaced by those regions which are not illuminated.

It is also possible however to generate a light pattern which has offset or axially offset "blocks of light". Two conductive tracks arranged directly one above the other, or their strips of light, can for example be identically operated, with the following conductive tracks or their strips of light being correspondingly operated with an axial offset thereto so that a the [sic] pulsating block of light is projected by the two upper conductive tracks beneath the non-illuminated region underneath this and such that a strip pattern that is offset when viewed in axial direction is projected. Instead of four conductive tracks, fewer (for example two) or more (for example five) conductive tracks can also be arranged one above the other. Depending on the surface property it is helpful for the individual strips of light together to generate a light pattern which can be reliably evaluated so that even with a dull or rough surface a container seam can be accurately pinpointed. It is also possible for each individual light source to be operated and not just the columns of light sources. Thus it can arise that a single conductive track or a plurality of conductive tracks is/are provided such that a variably producible light pattern can be projected onto the container wall region by variable actuating of the light sources.

The advantageously executed detection system/the inspection method can in the sense of the invention not only be used to determine the position of the container seam however. Since the illuminating unit is formed from a plurality of individually selectively operable strips of light, it can also be favourably used to detect external design features, so-called embossings. In this case an optical lens in front of the respective cameras can be dispensed with; the illuminating unit can be used as a dark-field illumination. As before, a strip-shaped light pattern is projected onto the container. Like the bottle seam, the embossing brings about a change on the container surface. The structure and form of the embossing is reflected by the projection. The (optical) detection system can be taught these structures as a function of the rotational position of the container. In this way the detection system is advantageously capable of determining an absolutely exact position of the embossing irrespective of content and container colour. Highlights of the strip pattern that is projected onto the container do not occur in the case of a surface that is smooth, i.e. one with no embossing. To the (optical) detection system the surface appears black. However if the strip pattern projected onto the container strikes the embossing or the elevations, then these highlights occur and are recorded by the optical assembly or by the cameras as (white) points of light. Between the highlights, the smooth container surface appears black so that the camera array can detect the entire embossing by way of the highlights. An alignment for the correct, i.e. aligned applying of the label relative to the embossing is possible by way of the detecting of the embossing.

BRIEF DESCRIPTION OF THE FIGURES

Further advantageous embodiments of the invention are disclosed in the dependent claims and the following description of the Figures. In the figures:

DETAILED DESCRIPTION

Figure 1:
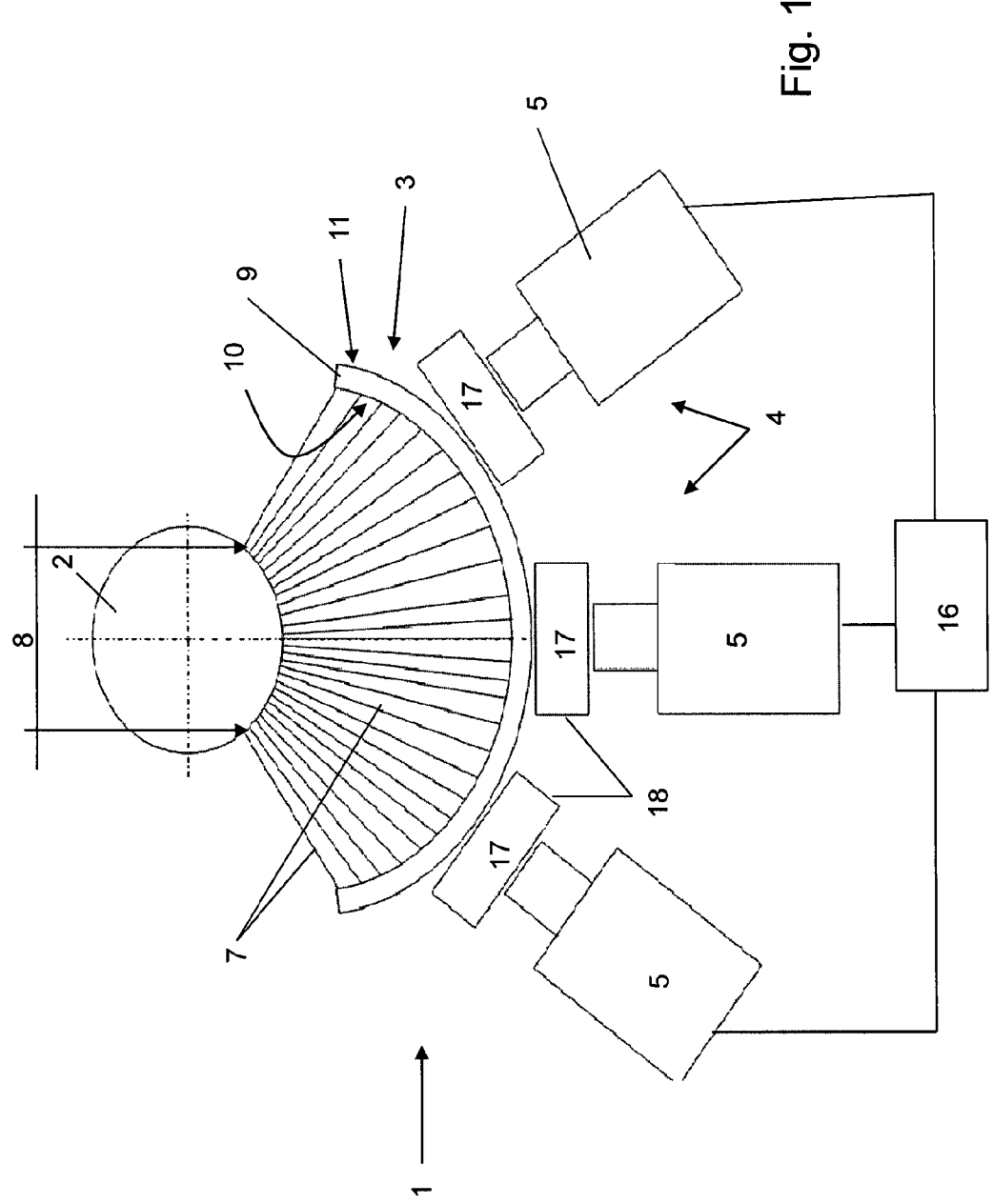
FIG. 1 shows a basic configuration of a detection system.

In the different figures, identical parts are identified by the same reference characters in each case, which is why they are usually described only once.

FIG. 1 shows a detection system 1 for detecting bottles 2 or similar containers. The exemplary bottles 2 can exhibit features such as for example bottle seams and/or design features, so-called embossings, arranged on their container wall. Detection system 1 exhibits at least one illuminating unit 3 and at least one optical assembly 4 having at least one camera 5.

Illuminating unit 3 exhibits a plurality of light sources 6 disposed in columns 14 (FIG. 2) and is configured so that a strip-shaped light beam 7 is projected onto a container wall region 8; the strip-shaped light beams 7 are each projected onto container wall region 8 at a distance from one another. Illuminating units 3 that are drawn with an unbroken line are stand [sic] for illuminating units 3 that are switched on, i.e. illuminating, while the illuminating units drawn with a broken line represent illuminating units 3, in this case diodes, which are switched off, i.e. not illuminating.

Containers or bottles 2 may consist of a transparent, translucent or opaque material and exhibit a preferably shiny surface. Bottle 2 can exhibit different colours and be filled with different filling media. However containers or bottles 2 may also exhibit a surface property that is different from a shiny surface property, for example a dull or rough surface.

In the case of the embodiment depicted in FIG. 1, illuminating unit 3 exhibits a carrier element 9 having a light surface 10 oriented towards container 2 and an opposite reverse side 11. Carrier element 9 is executed for example as a strip of sheet metal in the shape of a sector of a circle. Other suitable materials can of course also be used to embody carrier element 9.

Figure 2:
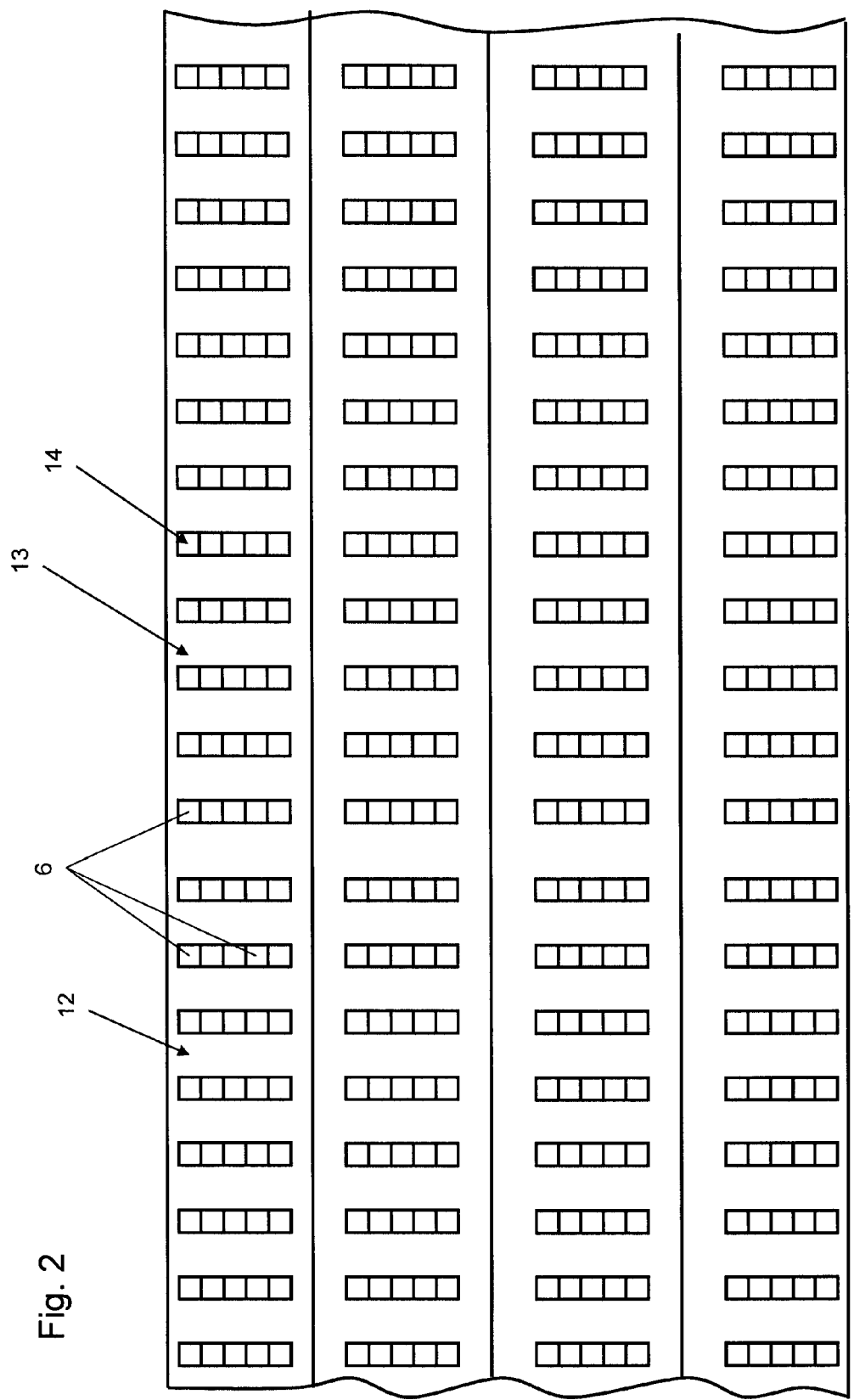
FIG. 2 shows a plurality of conductive tracks arranged one above the other as a detail, FIG. 3 shown an actuating example for generating a two-two block pattern with offset.

In the depicted example a plurality of conductive tracks 12, e.g. four conductive tracks 12, are arranged one above the other on the light surface 10 (FIG. 2). It is of course possible for light surface 10 to be formed from a single large conductive track or horizontally split conductive tracks. Each conductive track 12 is executed as a flexible conductive track 12 and exhibits vertically arranged recording strips 13 which are at a distance from one another when viewed in a longitudinal direction of conductive track 12. Light sources 6 can be disposed on recording strips 13. Strips of light (columns 14 of light sources 6) are formed in this way. Conductive track 12 can be connected by its reverse side to the light surface of carrier element 9.

A strip-shaped light pattern 15 is projected onto container wall region 8 (FIGS. 7 to 13) with conductive track 12, or with light sources 6 arranged thereon in vertical columns 14 or lines.

It is expedient if individual columns 14 or lines with the correspondingly arranged light sources 6 can be operated independently of one another, i.e. optionally switched on or off, so that a variably adjustable light pattern 15 can be projected onto container wall region 8. The respectively advantageous light pattern 15 can be generated variably as a function of the surface properties of the container or bottle 2.

Figure 7:
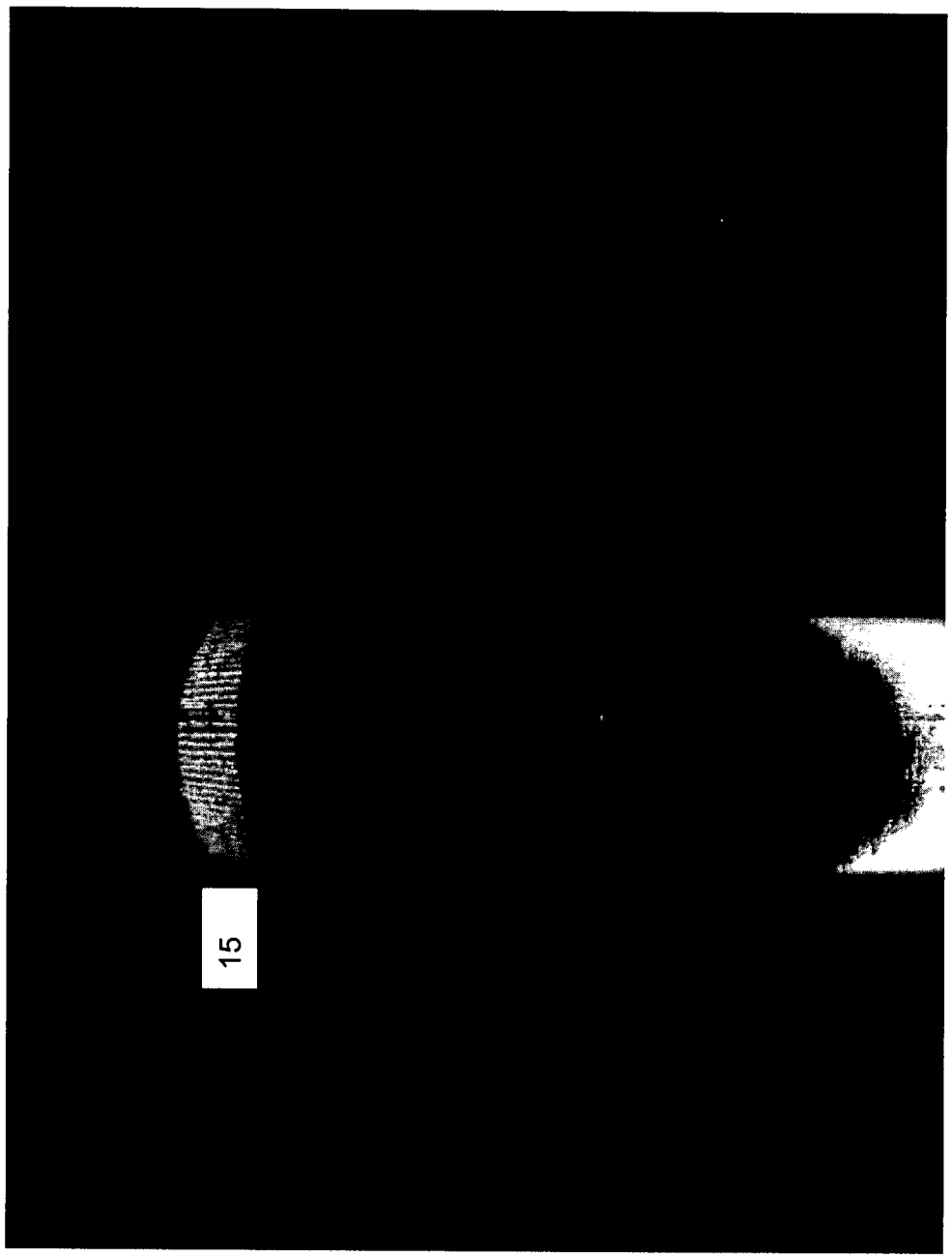
FIG. 7 shows a strip pattern as a projection onto a bottle with detrimental surface property.

An exemplarily strip-shaped light pattern 15 which is projected onto a preferably cylindrically configured container wall region 8 is shown in FIG. 7. Light beams 7, or strip-shaped light pattern 15, is shown as a light area, whereas the non-illuminated container wall appears black or dark.

As can be seen, light beams 7 which are adjacent to one another are very blurred, i.e. out of focus, or even partly merge one into the other, as a result of which an inspection task relating, for example, to a bottle seam that must be detected can be subject to error. Such an image occurs for example in a container wall region 8 that has a relatively rough surface. Light beams which are sharp, i.e. clearly demarcated from one another, could be projected on a container wall region 8 having a smooth surface.

This is where the invention comes in.

As previously mentioned, a plurality of—by way of example only—four conductive tracks 12 are arranged on carrier element 9, as depicted by way of example in FIG. 2. Conductive tracks 12 are arranged with their vertically disposed columns 14 linearly one above the other so as to create a strip of light which as it were extends from top to bottom and as it were appears continuous without division, and which is axially spaced from the adjacent strip of light.

Figure 3:
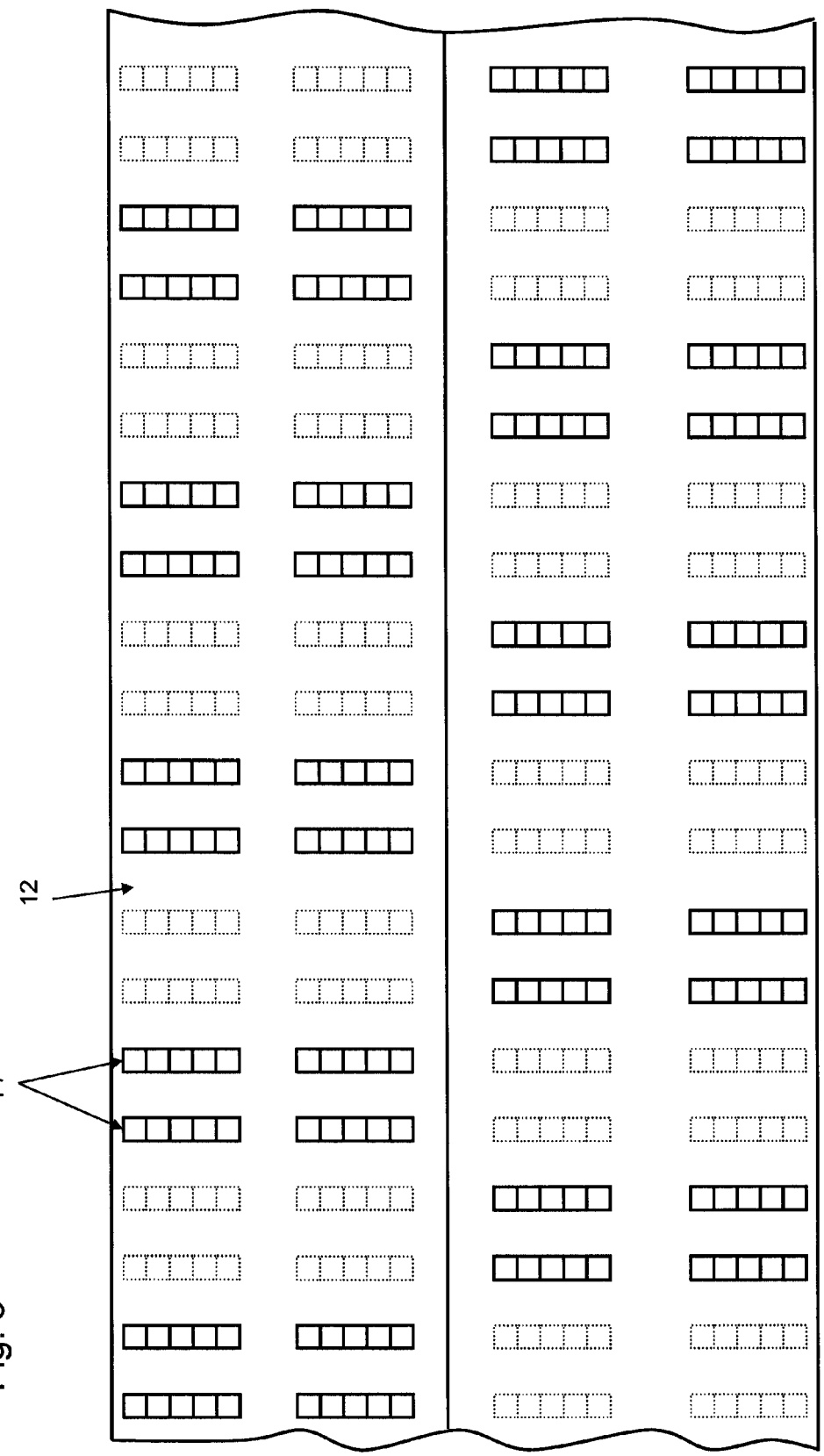
Figure 8:
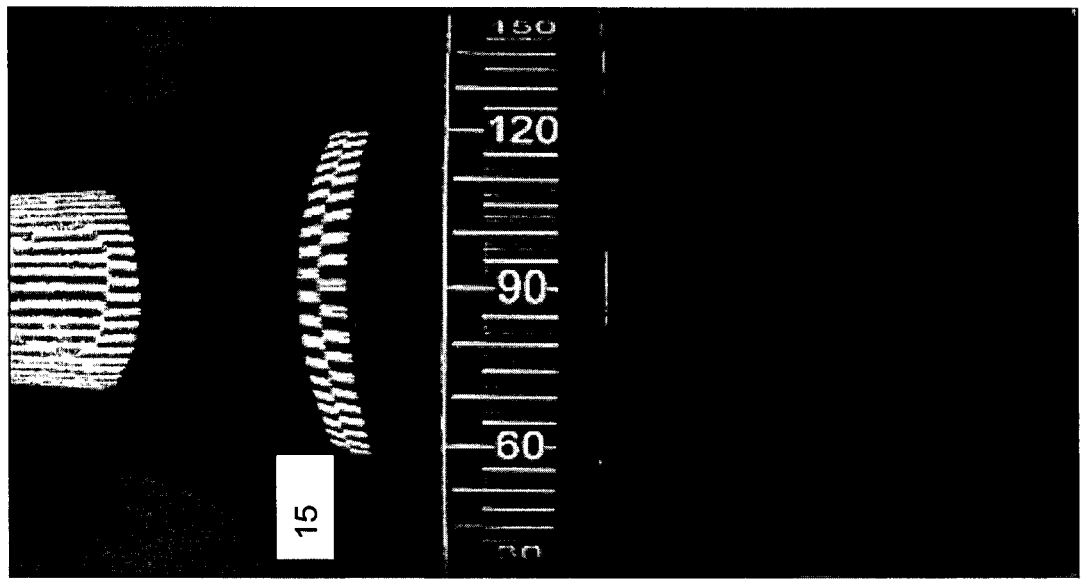
FIG. 8 shows a strip pattern as a projection according to the actuating example from FIG. 3.

In the case of projected light beams 7 depicted in FIG. 7, all columns 14 are switched on. If however it is detected beforehand that bottle 2 or container wall region 8 exhibits a surface property which can lead to a blurred projection of light beams, then individual columns 14 are operated such that for example two columns 14 which are arranged immediately adjacent to and above one another are activated simultaneously, while columns 14 which are immediately adjacent and arranged thereunder are deactivated. Such a variable switching arrangement of conductive tracks 12 is shown in FIG. 3. FIG. 8 shows the projected light beams/projected light pattern 15 on container wall region 8 brought about by the switching according to FIG. 3. It can be seen that as it were a two-two light block pattern can be projected in offset arrangement onto container wall region 8. The light pattern projected in FIG. 8 is undisturbed which means that there is no bottle seam in container wall region 8 concerned. Such a bottle seam can be seen in FIG. 9 as a disturbance in the light pattern; the bottle seam is emphasised by a detection strip shown for demonstration purposes only.

It should be noted here that according to the actuating of columns 14 as shown in FIG. 3, the light pattern has very sharp contours which can be projected even onto a container which has a relatively rough surface. The immediately adjacent strips of light may merge with one another somewhat or blur, but the generated block of light can be advantageously and reliably inspected for disturbances because the region which is not illuminated distances it sufficiently from the next block of light. Consequently disturbances are inspected not by line but by block with the invention.

Figure 4:
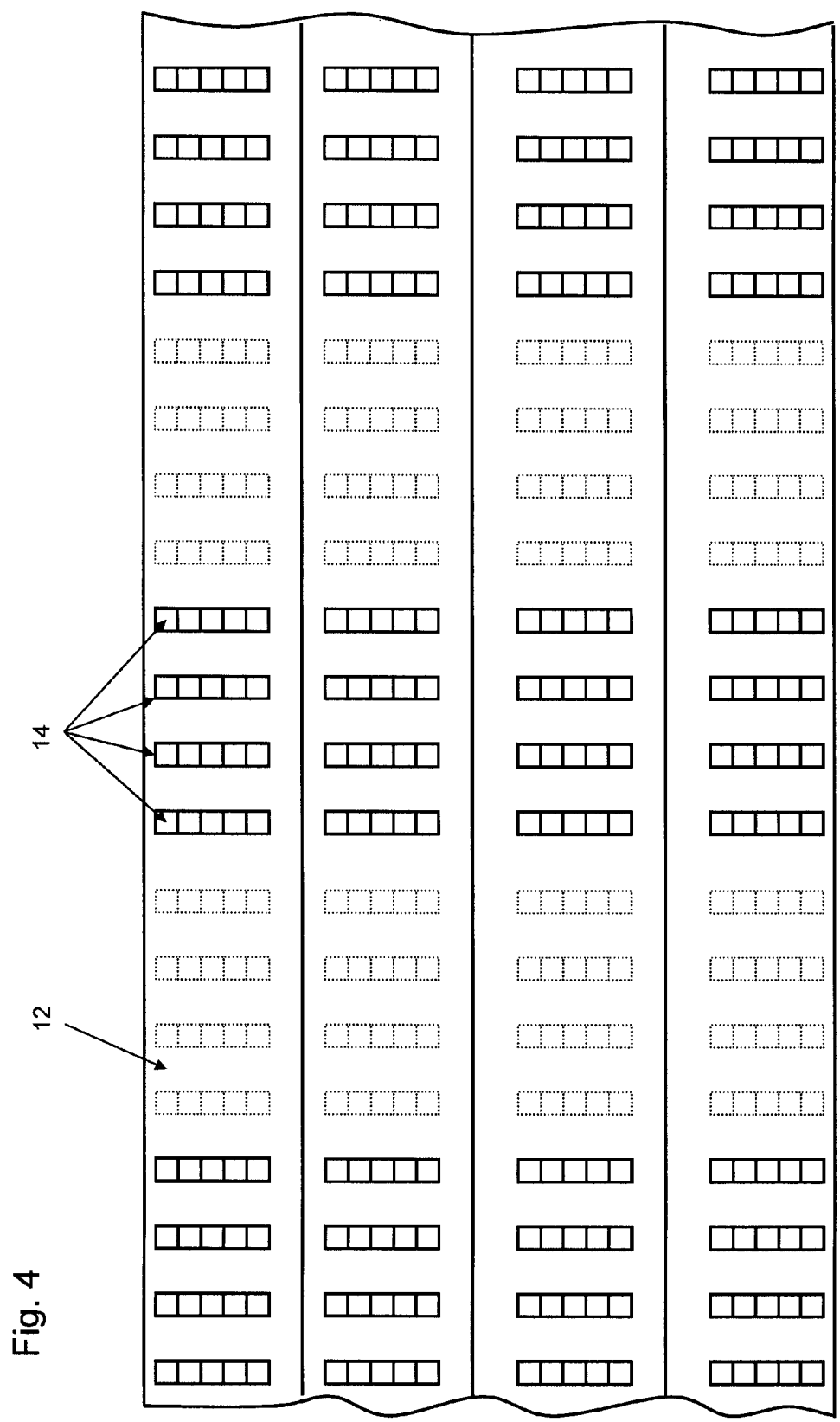
FIG. 4 shows an actuating example for generating a four-four block line pattern without offset.
Figure 10:
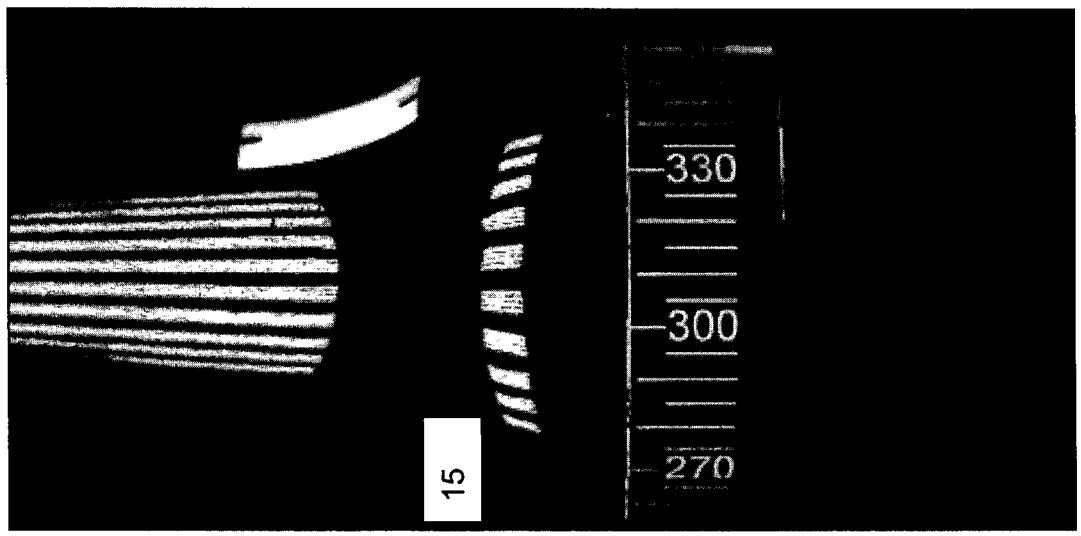
FIG. 10 shows a strip pattern as a projection according to the actuating example from FIG. 4.

A further possible actuating variant of columns 14 is shown in FIG. 4; in this case by way of example four columns 14 arranged immediately adjacent to and above one another are switched on simultaneously, with the four columns 14 immediately adjacent to each of them being switched off. FIG. 10 shows the corresponding projected light pattern. It can be seen that an as it were four-four light line pattern in a non-offset arrangement can be projected onto container wall region 8.

In FIG. 10 is the light pattern is not disturbed. FIG. 11 again shows a disturbance in the light patterns by the bottle seam. Here again it should be noted that the detection strip is shown for demonstration purposes only.

Figure 5:
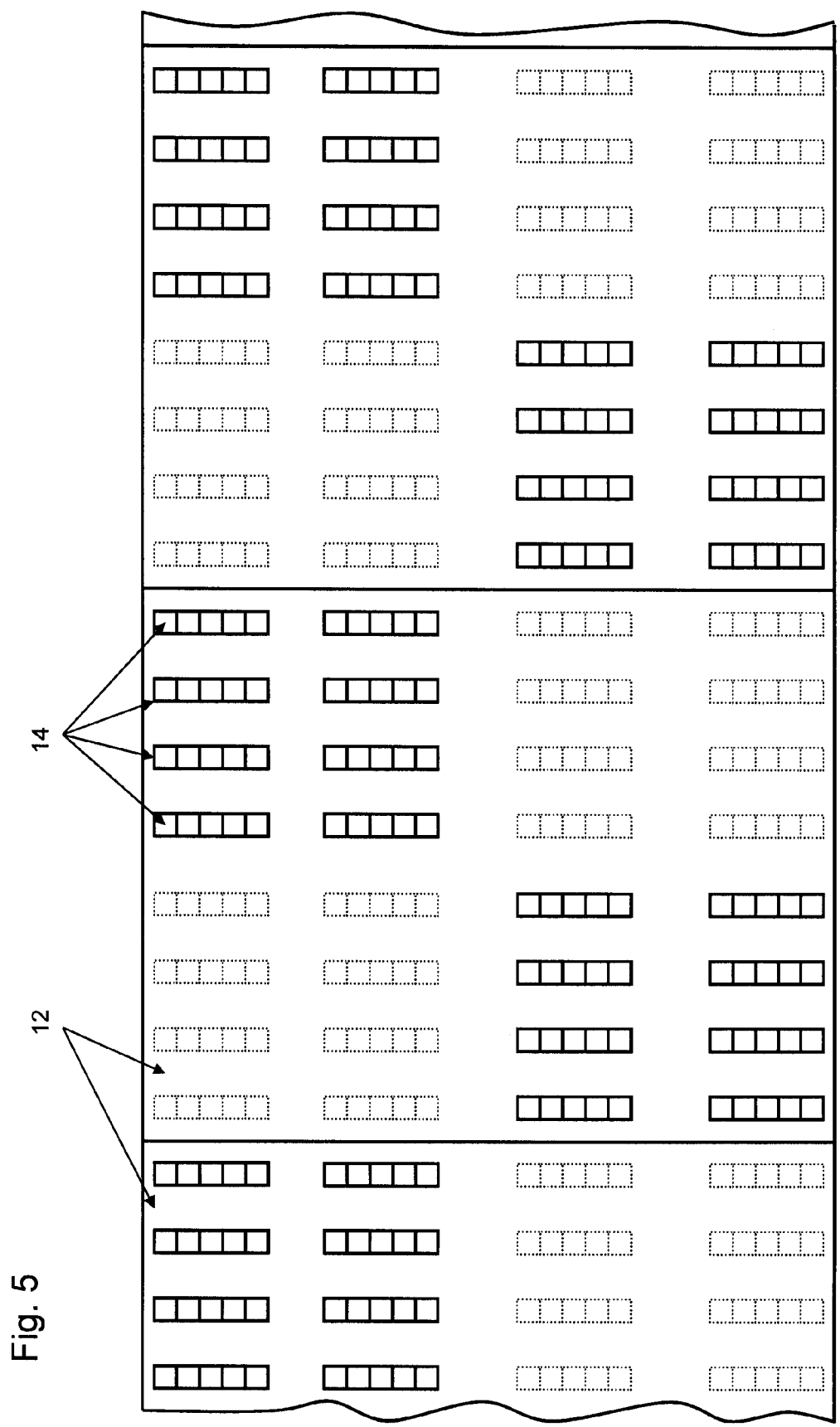
FIG. 5 shows a actuating example for generating a four-four block line pattern with offset.
Figure 12:
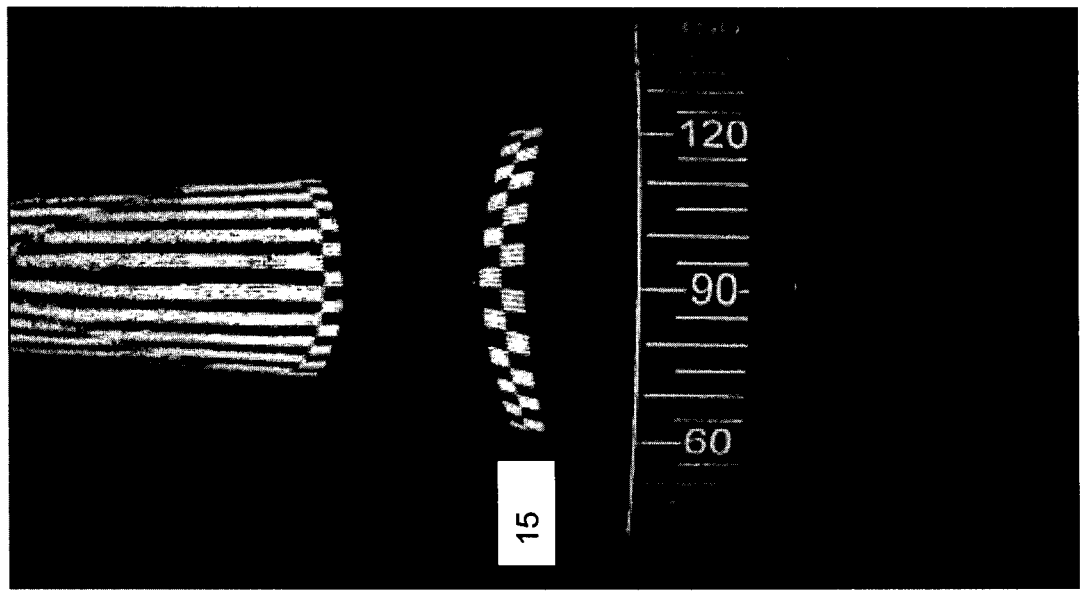
FIG. 12 shows a strip pattern as a projection according to the actuating example from FIG. 5.

FIG. 5 in turn shows a light pattern also variably adjusted to surface properties of the container; here by way of example, four columns 14 arranged immediately adjacent to and above one another are simultaneously switched on while the four columns 14 immediately adjacent to and beneath them are switched off. It can be seen that an as it were four-four light block pattern in an offset arrangement can be projected onto container wall region 8. The blocks below are axially offset from the blocks above. The corresponding projected light pattern is shown in FIG. 12. The advantage of a block of light being generated axially offset to the others is evident here such that, unlike a light block pattern with no offset, blocks of light are projected onto the entire periphery of container wall region 8.

Figure 6:
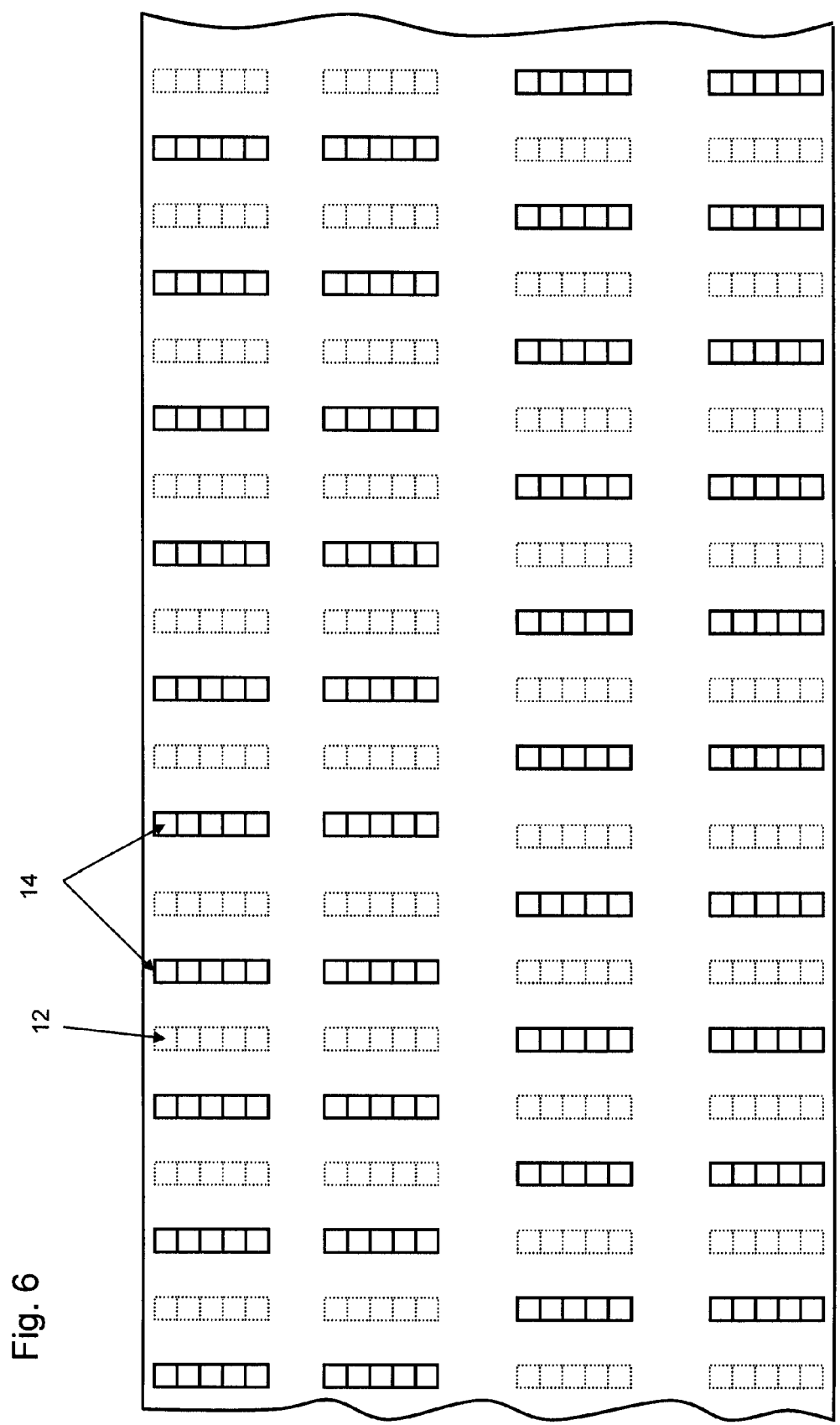
FIG. 6 shows an actuating example for generating a one-one line pattern with offset.
Figure 13:
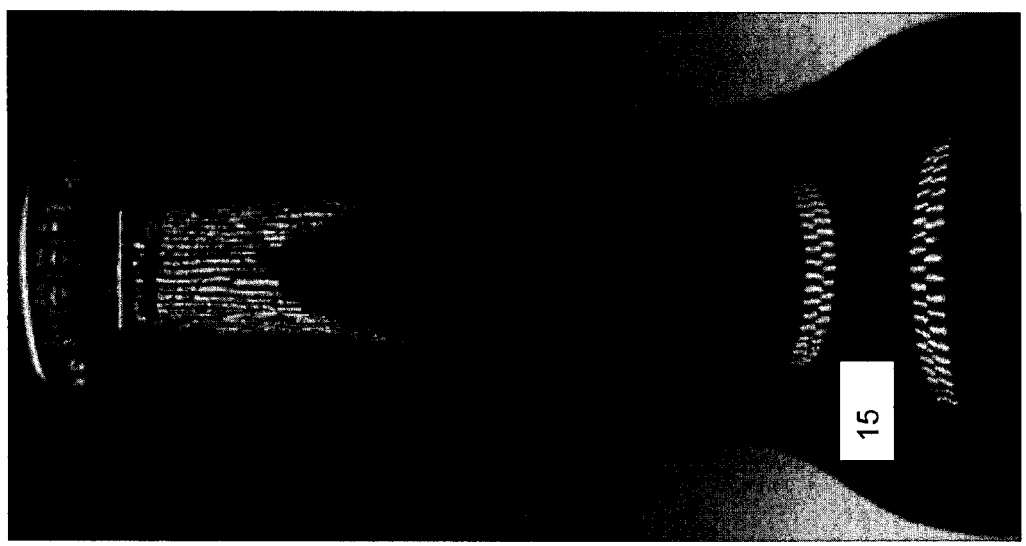
FIG. 13 shows a strip pattern as a projection according to the actuating example from FIG. 6.

FIG. 6 in turn shows a light pattern 15 likewise variably adjusted to surface properties of the container or bottle 2 and in which by way of example each of a column 14 arranged immediately adjacent to and above one another is simultaneously activated while the column 14 immediately adjacent and arranged thereunder is deactivated. To this extent the term "block of light" in the sense of the invention is also understood to mean that activated strips of light directly alternate with deactivated strips of light, it being possible to project lower lines axially offset to upper lines, or without offset, onto container wall region 8. The projected light pattern which corresponds to FIG. 6 is shown in FIG. 13.

It is advantageous when two of conductive tracks 12, preferably conductive tracks 12 which are arranged immediately one above the other, are always switched with the same switching arrangement, i.e. columns 14 are identically activated in their axial sequence. It is of course possible to provide more or fewer than four conductive tracks 12. It is expedient that when a detrimental surface quality is detected, the individual strips of light are activated such that as it were a "block" light pattern is generated whose individual blocks can be inspected for anomalies.

The advantage of an invention which can provide a variably producible light pattern that can be produced as a function of surface properties of containers or bottles 2, and in which columns 14 of conductive tracks 12 are activated, i.e. switched on, or not, i.e. switched off, is evident.

According to the invention, the appropriate actuating of individual columns 14 is effected by way of a control unit 16 which can be configured as an evaluation and control unit 16. To this end, light pattern 15 which is required as a function of the surface properties of the container is advantageously stored in evaluation and control unit 16 and can be easily called or activated. The required light pattern 15 can of course also be manually entered and preferably stored in evaluation and control unit 16. It is possible for the surface properties of the containers to be automatically or manually fed, by way of suitable devices, into evaluation and control unit 16 which then fully automatically or by manual call of the associated required light pattern 15 generates such a light pattern by actuating light sources 6 or columns 14.

Container 2 according to the embodiment shown in FIG. 1 can transported [sic] past detection system 1 in a labelling star wheel of a labelling machine. It is therefore advantageous for carrier element 9 to be configured so that it does not impinge on the transport path (circular path) of container 2. In this way, illuminating unit 3 can project a variable strip-shaped light pattern 15 onto a container wall region 8 which corresponds to about 40% of the whole periphery of container 2.

Detection system 1 according to the invention can of course be used on any container treatment device and not just on labelling machines.

Optical assembly 4 (FIG. 1) exhibits three cameras 5 as depicted by way of example. Cameras 5 are arranged vertically offset relative to illuminating unit 3. This means that optical assembly 4 can be disposed above or below illuminating unit 3. Optical assembly 4 is disposed such that container wall region 8 which is illuminated by the strip-shaped light pattern can be recorded. Optical assembly 4, i.e. each camera 5, is connected to evaluation and control unit 16 in which the images or image data supplied by respective camera 5 are evaluated. An evaluation by way of a computer-programmable programme that can be run in evaluation and control unit 16 is also possible. The processing of the images or image data supplied by camera 5 is effected for example by comparison with nominal data stored in evaluation and control unit 16. To this extent evaluation and control unit 16 may also be referred to as image processing and control unit 16. Evaluation and control unit 16 is for example a processor or a computerised unit having corresponding inputs for analogue or digital data supplied by the respective camera. Evaluation and control unit 16 also exhibits outputs (not shown) which are connected to individual components (e.g. container alignment, labelling unit) of the exemplary labelling machine.

Only one illuminating unit 3, seen in plan view, is visible in the embodiment depicted in FIG. 1. It is possible to arrange an identical or different illuminating unit 3 below or above the visible illuminating unit 3, in which case camera 5 would be disposed between both illuminating units 3. Illuminating unit 3 that is arranged either above or below can also exhibit columns 14 of light sources 6, i.e. strips of light, which can be actuated accordingly. Illuminating units 3 arranged one above the other can be adjustable, for example height-adjustable, together and/or simultaneously.

An optical lens 17 is associated with each camera 5 by way of example only. In the embodiment depicted in FIG. 1, respective optical lens 17 is configured as a cylindrical lens arranged with its end faces 18 at right angles to the lenses of respective camera 5. Optical lens 17 may also be configured as a Fresnel lens, to name just one further example.

Figure 9:
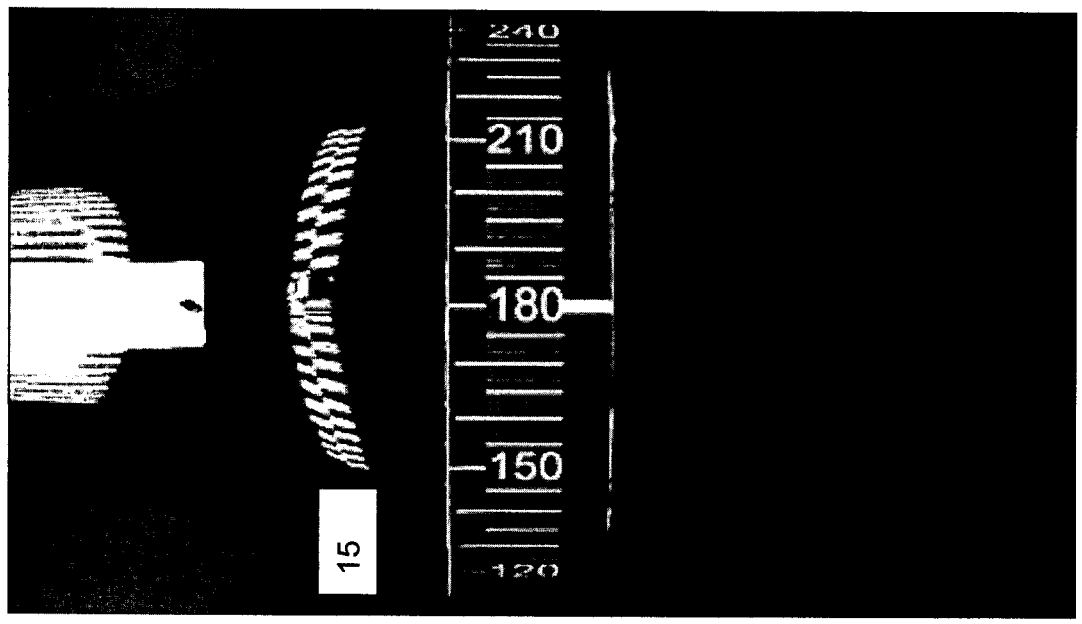
FIG. 9 shows a strip pattern as a projection according to the actuating example from FIG. 3 with disturbance.
Figure 11:
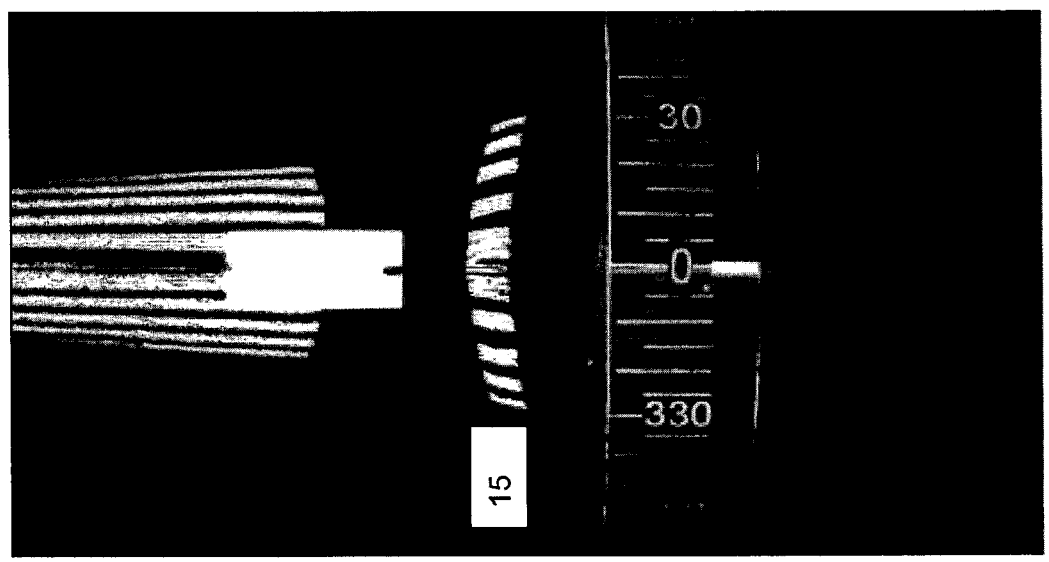
FIG. 11 shows a strip pattern as a projection according to the actuating example from FIG. 4 with disturbance.

Because of the special actuating of individual light sources 6 (strips or columns 14), a targeted vertical, variably adjustable strip pattern 15 is projected into the container body or onto container wall region 8 concerned in this way. If no changes such as for example a bottle seam are present on the container wall or on container wall region 8 that is to be inspected, then columns 14 or the lines or blocks of vertical strip pattern 15 (FIGS. 8,10,12,13) are always aligned the same way relative to one another in number irrespective of container rotations or container positions. If the bottle seam now encroached on this line or block pattern (strip-shaped light pattern 15), the relative number and arrangement of the projected strips of light of the block of light concerned will change (FIGS. 9,11). A change would occur for example in the line or block imaging. In this way an absolutely accurate position of the container seam or bottle seam can be advantageously determined with the invention irrespective of surface quality, container content and container colour.

Two detection systems 1 in sequence can be favourably provided so that by rotating the container an accurate determination of the position of the container seam is ensured, this not least because, as described above, detection system 1 should not engage with a labelling star wheel where one is provided, and especially not by its carrier element 9. A further container wall region 8 can be inspected with the following second detection system by rotating container 2. Here the invention is based on the fact that the container stands upright on a rotatable turntable and can be rotated as it is being fed to detection system 1. A detection system for fine alignment can be provided as well as a detection system for rough alignment.

Figure 14:
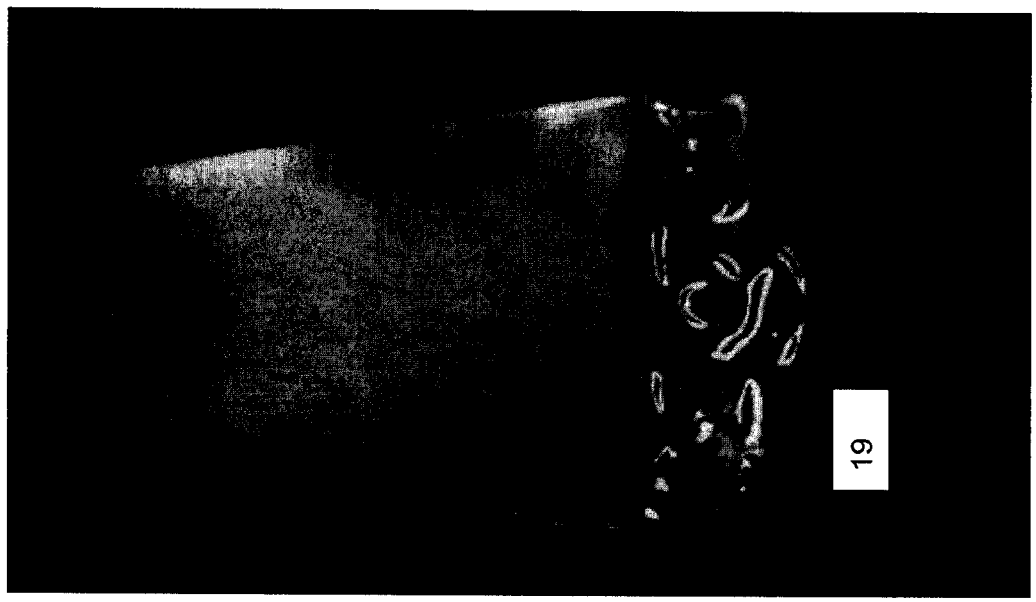
FIG. 14 shows a projection of the strip pattern for detecting an embossing.

As can be seen from FIG. 14, detection system 1 may also be used to detect external design features, so-called embossings 19, because illuminating unit 3 exhibits a plurality of individually selectively operable light sources 6 or columns 14. In this case an optical lens in front of the respective cameras 5 can be dispensed with; the illuminating unit 3 can be used as a dark-field illumination. As before, a strip-shaped light pattern 15 is projected onto the container in this case. Like the bottle seam, embossing 19 produces a change on the container surface. These structures can be taught to (optical) detection system 1 depending on the rotational position of container 2. Detection system 1 is in this way advantageously able to determine an absolutely accurate position of embossing 19 irrespective of content, surface property and container colour. In the case of a smooth surface, i.e. one with no embossing, no highlights of strip pattern 15 that is projected onto the container occur. The surface appears black or dark (conversely white or light) to (optical) detection system 1. If however strip pattern 15 that is projected onto container 2 strikes the embossing or the elevations, these highlights occur and are recorded by the optical assembly or by the cameras as (white or light) points of light (conversely black or dark points of light). Between the highlights, the smooth surface of the container appears black or dark (conversely white or light) so that the entire embossing 19 can be detected by way of the highlights of optical arrangement 4. An alignment for the correct, i.e. aligned, applying of the label relative to embossing 19 is possible by way of the detecting of embossing 19. It is expedient in this case for all columns 14 of illuminating unit 3 to be actuated, i.e. switched on, so as to obtain the highlights. Preferably use will be made here of the advantageous embodiment where two illuminating units 3 are arranged one above the other, in which case, for example, always the lower illuminating unit could be used for detecting the embossing, and with the upper illuminating unit 3, reacting to the surface property of bottle 2, projecting the selectively operable/variably adjustable light pattern 15 onto container wall region 8.

LIST OF REFERENCE SIGNS

1 Detection system
2 Container/bottle
3 Illuminating unit
4 Optical assembly
5 Camera
6 Light source
7 Light beams
8 Container wall region
9 Carrier element
10 Light surface
11 Reverse side of 9
12 Conductive track
13 Recording strips
14 Vertical columns or lines
15 Vertical light pattern
16 Evaluation and control unit
17 Optical lens
18 End faces of 17
19 Embossing

The invention claimed is:

1. An apparatus comprising a system for detecting containers that exhibit features arranged on a container wall thereof, said system comprising an optical assembly comprising a camera, and an illuminating unit comprising a plurality of light sources arranged on a plurality of conductive tracks, said light sources, when viewed in a vertical direction of said illuminating unit, being arranged one above the other in vertical columns such that said light sources project a strip-shaped light beam onto a container-wall region of said container wall, said projected strip-shaped light beams being disposed at a distance from one another when viewed in an axial direction of said illuminating unit, wherein said light sources, are, when viewed in axial direction, arranged on said conductive track one above the other without offset, wherein each vertically aligned column of light sources is actuated via a control unit that is configured such that said vertically aligned columns project a light pattern onto said container-wall region that is variably adjusted as a function of surface properties of said container-wall region, said illuminating unit comprising a first light source set on a first vertically aligned column and a second light source set on a second vertically aligned column that is horizontally adjacent to said first vertically aligned column, each of said first and second light source sets comprising at least one light source, wherein said adjustment is effected by switching said first light source set between an on state and an off state concurrently with switching said second light source set between an on state and an off state.

2. The apparatus of claim 1, wherein at least one light source set of a column can be switched on, and at least light source set can be switched off in the vertical direction.

3. The apparatus of claim 1, wherein said light source groups are controlled to project a chessboard-like pattern of light and dark zones on said container-wall region.

4. The apparatus of claim 1, wherein said illuminating unit comprises a carrier element having a light surface oriented toward said container.

5. The apparatus of claim 1, wherein said illuminating unit is configured to project a vertically aligned strip pattern onto said container-wall region.

6. The apparatus of claim 1, wherein said plurality of conductive tracks is on a light surface of said illuminating unit.

7. The apparatus of claim 1, wherein said illuminating unit is configured, at least on a light surface thereof, as a sector of a circle.

8. The apparatus of claim 1, wherein said optical assembly comprises a plurality of cameras.

9. The apparatus of claim 1, further comprising an optical lens associated with said camera.

10. The apparatus of claim 1, wherein said camera is arranged between two illuminating units arranged vertically one above the other.

11. The apparatus of claim 1, wherein said illuminating unit is height-adjustable together and/or simultaneously with said camera.

12. The apparatus of claim 1, further comprising a labeling machine for labeling said container.

13. A method comprising inspecting containers using an apparatus that comprises a system for detecting containers that exhibit features arranged on a container wall thereof, said system comprising an optical assembly comprising a camera, and an illuminating unit comprising a plurality of light sources arranged on a plurality of conductive tracks, said light sources, when viewed in a vertical direction of said illuminating unit, being arranged one above the other in vertical columns such that said light sources project a strip-shaped light beam onto a container-wall region of said container wall, said projected strip-shaped light beams being disposed at a distance from one another when viewed in an axial direction of said illuminating unit, wherein said light sources, are, when viewed in axial direction, arranged on said conductive track one above the other without offset, wherein each vertically aligned column of light sources is actuated via a control unit that is configured such that said vertically aligned columns project a light pattern onto said container-wall region that is variably adjusted as a function of surface properties of said container-wall region, said illuminating unit comprising a first light source set on a first vertically aligned column and a second light source set on a second vertically aligned column that is horizontally adjacent to said first vertically aligned column, each of said first and second light source sets comprising at least one light source, wherein said adjustment is effected by switching said first light source set between an on-state and an off-state concurrently with switching said second light source set between an on-state and an off-state, wherein inspecting containers comprises detecting surface properties of a container, and causing a control unit to actuate each vertically aligned column of light sources as a function of said detected surface properties such that said columns project, onto said container-wall region, a light pattern that is variably adjusted as a function of said surface properties.

14. The method of claim 13, wherein causing said control unit to actuate comprises causing said vertically aligned columns of light sources of each conductive track to be actuated such that a strip pattern without offset is projected onto said container-wall region.

15. The method of claim 13, wherein causing said control unit to actuate comprises causing said vertically aligned columns of light sources of each conductive track to be actuated such that a strip pattern projected onto said container-wall region exhibits offset when viewed in an axial direction.

16. The method of claim 13, further comprising detecting container seams.

17. The method of claim 13, further comprising detecting embossing on said container.

18. The method of claim 13, further comprising labeling said container.

* * * * *